(12) United States Patent
Liu et al.

(10) Patent No.: US 10,206,582 B2
(45) Date of Patent: Feb. 19, 2019

(54) HUMAN SLEEP MONITORING DEVICE AND MONITORING METHOD THEREOF

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Yingming Liu, Beijing (CN); Xue Dong, Beijing (CN); Xiaochuan Chen, Beijing (CN); Haisheng Wang, Beijing (CN); Xiaoliang Ding, Beijing (CN); Shengji Yang, Beijing (CN); Weijie Zhao, Beijing (CN); Hongjuan Liu, Beijing (CN); Changfeng Li, Beijing (CN); Wei Liu, Beijing (CN); Xuewen Lv, Beijing (CN); Jing Zhao, Beijing (CN); Xuebo Zhang, Beijing (CN); Rui Xu, Beijing (CN); Lei Wang, Beijing (CN); Ming Yang, Beijing (CN); Liguang Deng, Beijing (CN); Huizhong Zhu, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

(*) Notice: Subject to any disclaimer, the term of this patent is extended or adjusted under 35 U.S.C. 154(b) by 243 days.

(21) Appl. No.: 15/300,897

(22) PCT Filed: Dec. 31, 2015

(86) PCT No.: PCT/CN2015/100135
§ 371 (c)(1),
(2) Date: Sep. 30, 2016

(87) PCT Pub. No.: WO2017/031907
PCT Pub. Date: Mar. 2, 2017

(65) Prior Publication Data
US 2017/0181635 A1 Jun. 29, 2017

(30) Foreign Application Priority Data

Aug. 21, 2015 (CN) .......................... 2015 1 0521048

(51) Int. Cl.
*A61B 6/00* (2006.01)
*A61B 5/00* (2006.01)
(Continued)

(52) U.S. Cl.
CPC .......... *A61B 5/0082* (2013.01); *A61B 5/4806* (2013.01); *A61B 5/4836* (2013.01);
(Continued)

(58) Field of Classification Search
CPC .......... A61B 2562/0233; A61B 5/0082; A61B 5/0261; A61B 5/4806; A61B 5/4836;
(Continued)

(56) References Cited

U.S. PATENT DOCUMENTS

2007/0233208 A1* 10/2007 Kurtz .................. A61N 5/0613
607/88
2010/0262026 A1 10/2010 Meftah et al.
(Continued)

FOREIGN PATENT DOCUMENTS

| CN | 101896120 A | 11/2010 |
|---|---|---|
| CN | 102750015 A | 10/2012 |

(Continued)

OTHER PUBLICATIONS

The Fourth Chinese Office Action dated Oct. 25, 2017; Appln. 201510521048.1.
(Continued)

*Primary Examiner* — George Manuel
(74) *Attorney, Agent, or Firm* — Ladas & Parry LLP

(57) ABSTRACT

A human sleep monitoring device, including a signal processing module (5), a reflecting film (3), a detection light
(Continued)

emitting module (1) and a receiving module (4), wherein the detection light emitting module (1) is configured to emit detection light to the human body; the reflecting film (3) is configured to guide light, which is emitted by the detection light emitting module and not absorbed by the human body, to the receiving module (4); the receiving module (4) is configured to receive the light guided by the reflecting film (3); and the signal processing module (5) is configured to obtain physiological sign data of the human body according to intensity information of the light received by the receiving module (4). The device can monitor the sleep state of the human body in real time, and improve body sleep quality. A human sleep monitoring method is also provided.

16 Claims, 2 Drawing Sheets

(51) Int. Cl.
*A61N 5/06* (2006.01)
*A61B 5/026* (2006.01)
*A61H 39/00* (2006.01)

(52) U.S. Cl.
CPC ............ *A61B 5/6829* (2013.01); *A61B 5/746* (2013.01); *A61B 5/7455* (2013.01); *A61N 5/0619* (2013.01); *A61B 5/0261* (2013.01); *A61B 2562/0233* (2013.01); *A61H 39/00* (2013.01); *A61N 2005/0663* (2013.01)

(58) Field of Classification Search
CPC ..... A61B 5/6829; A61B 5/7455; A61B 5/746; A61H 39/00; A61N 2005/0663; A61N 5/0619
See application file for complete search history.

(56) References Cited

U.S. PATENT DOCUMENTS

| | | | |
|---|---|---|---|
| 2012/0101344 A1* | 4/2012 | Desjardins | A61B 5/0059 600/300 |
| 2013/0253338 A1* | 9/2013 | Kang | A61B 5/0071 600/477 |

FOREIGN PATENT DOCUMENTS

| | | |
|---|---|---|
| CN | 103608854 A | 2/2014 |
| CN | 104257368 A | 1/2015 |
| CN | 104783950 A | 7/2015 |
| CN | 105078414 A | 11/2015 |
| CN | 205107620 U | 3/2016 |
| JP | 11188009 A | 7/1999 |

OTHER PUBLICATIONS

International Search Report and Written Opinion dated Apr. 26, 2016; PCT/CN2015/100135.
First Chinese Office Action dated Jul. 4, 2016; Appln. No. 2015102521048.1.
The Third Chinese Office Action dated Aug. 2, 2017; Appln. No. 201510521048.1.
Second Chinese Office Action dated Mar. 2, 2017; Appln. No. 201510521048.1.

* cited by examiner

HUMAN SLEEP MONITORING DEVICE AND MONITORING METHOD THEREOF

TECHNICAL FIELD

Embodiments of the present disclosure relate to a human sleep monitoring device and a monitoring method thereof.

BACKGROUND

The intelligent industry of monitoring field with the technology of the internet of things (IoT) will become one of important industries in the future. With the continuous development of economic globalization, the intelligent monitoring market has huge size. In the near future, the health monitoring industry will incorporate more artificial intelligence (AI), sensing technology and other high technology, so that the health monitoring service can be intelligentized in the true meaning and promote the prosperous development of medical industry. Under china's new medical reform background, intelligent monitoring is entering the lives of ordinary people.

Human sleep is the process of allowing various functions of the body to get enough rest and recovery, but incorrect sleeping posture will cause physical illness. For example, incorrect sleeping posture will result in the shortness of breath and potential risk of respiratory disease; incorrect sleeping posture will oppress the cervical spine and cause cervical spondylosis after a long time, and hence the physical health can be affected. In addition, poor sleep effect will also affect the recovery degree of various functions of the body and affect the physical health.

SUMMARY

Embodiments of the present disclosure provide a human sleep monitoring device and a monitoring method thereof, which can monitor the sleep state of the human body in real time and remind the user of converting the sleeping posture of the human body into normal sleeping posture.

According to embodiments of this disclosure, a human sleep monitoring device, comprising a signal processing module, an alarm module, a reflecting film, a detection light emitting module mounted on the reflecting film, and a receiving module, wherein the reflecting film is configured to guide light, which is emitted by the detection light emitting module and not absorbed by the human body, to the receiving module; the reflecting film comprises a human body contact surface making contact with the human body, and the human body contact surface is a illuminating surface; the detection light emitting module and the receiving module are mounted on a surface of the deviated human body contact surface of the reflecting film; and the deviated human body contact surface is a reflecting surface so as to fully reflect the part of the sensitive light in the reflecting film which irradiated into the reflecting film; the alarm module give an alarm when receiving a alarm signal; the signal processing module is signal connected with the receiving module and obtain systole data information according to intensity information of the sensitive light received by the receiving module and compare the obtained systole data information with the systole data information in the normal sleep state of the human body, and sends an alarm signal to the alarm module in response to abnormal obtained systole data information, and the alarm module gives an alarm when receiving alarm signal.

According to other embodiments of this disclosure, a monitoring method of the human sleep monitoring device, comprising: allowing the detection light emitting module to emit sensitive light, which can be absorbed by the human body, to the human body; allowing the sensitive light to run through the reflecting surface of the reflecting film, enter the reflecting film and be irradiated to the human body through a illuminating surface of the reflecting film, and allowing the human body blood absorbs the sensitive light, and allowing the sensitive light not absorbed by the human body get back to the reflect film and irradiates the reflecting surface, and is guided to a receiving module through fully reflection of the reflecting film; allowing the receiving module to transmit the intensity information of the received sensitive light to the signal processing module; and allowing the signal processing module to analyze the intensity information of the sensitive light, obtain the systole data information, and compare the obtained systole data information with the systole data information in the normal sleep state of the human body; send an alarm signal to the alarm module when the obtained systole data information is abnormal, and allowing the alarm module to give an alarm to remind the human body of correcting the sleeping state until the sleep state of the human body is normal.

According to embodiments of this disclosure, a human sleep monitoring device, comprising a signal processing module, a reflecting film, a detection light emitting module and a receiving module, wherein the detection light emitting module is configured to emit detection light to the human body; the reflecting film is configured to guide light, which is emitted by the detection light emitting module and not absorbed by the human body, to the receiving module; the receiving module is configured to receive the light guided by the reflecting film; and the signal processing module is configured to obtain physiological sign data of the human body according to intensity information of the light received by the receiving module.

For example, wherein the reflecting film comprises a human body contact surface making contact with the human body and a deviated human body contact surface not making contact with the human body; at least partial human body contact surface is a illuminating surface; an internal surface of the deviated human body contact surface is a reflecting surface; the detection light emitting module and the receiving module are mounted on an external surface of the deviated human body contact surface of the reflecting film; and the internal surface of the deviated human body contact surface fully reflects the light irradiated into the reflecting film on the internal surface.

For example, wherein the physiological sign data of the human body include systole data information; and the signal processing module compares the obtained systole data information with the systole data information in the normal sleep state of the human body, and obtains the health status information of the human body.

For example, further comprising an alarm module, wherein the signal processing module sends an alarm signal to the alarm module in response to abnormal obtained systole data information, and the alarm module gives an alarm according to the received alarm signal.

For example, wherein the signal processing module comprises: a photoelectric converter connected with the receiving module and configured to convert the intensity information of the light received by the receiving module into current intensity information; an amplifier connected with the photoelectric converter and configured to amplify the current information received by the photoelectric converter into recognizable degree; a data converter connected with the amplifier and configured to convert the amplified current information obtained by the amplifier into data information; and a data processing unit connected with the data converter and configured to process the information received by the data converter.

For example, further comprising an alarm module, wherein the data processing unit is connected with the alarm module and sends an alarm signal to the alarm module when determining that the sleep state of the human body is abnormal according to the data converted by the data converter.

For example, wherein the alarm module is a vibration alarm.

For example, wherein the detection light emitting module is an infrared emitter.

For example, wherein the human body contact surface of the reflecting film is used for covering the sole of the human body.

For example, wherein the detection light emitting module is mounted on a portion of the reflecting film disposed on the heel, and the receiving module is mounted on a portion of the reflecting film disposed on the toes.

For example, further comprising: at least one physiotherapy module mounted on the reflecting film, wherein each physiotherapy module is connected with the signal processing module; and the signal processing module is also configured to determine the health status of the human organ according to the information received by the receiving module, and control corresponding physiotherapy module to give a physical therapy to the sole when determining that an organ is diseased.

For example, wherein each physiotherapy module is a physiotherapy light emitting module.

For example, wherein each physiotherapy module is a massage module.

For example, wherein at least one physiotherapy module comprises a plurality of physiotherapy module, and each physiotherapy module is used for giving a physical therapy to one acupoint of the sole.

According to embodiments of this disclosure, a monitoring method of the human sleep monitoring device, comprising: allowing the detection light emitting module to emit light, which can be absorbed by the human body, to the human body; allowing the light emitted by the detection light emitting module to run through the surface of the reflecting film, enter the reflecting film and be irradiated to the human body through the reflecting film, and allowing the sensitive light not absorbed by the human body to be guided to the receiving module through the reflecting film; allowing the receiving module to transmit the intensity information of the received light to the signal processing module; and allowing the signal processing module to analyze the intensity information of the light, obtain the systole data information, and compare the obtained systole data information with the systole data information in the normal sleep state of the human body.

For example, further comprising: allowing the signal processing module to send an alarm signal to the alarm module when the obtained systole data information is abnormal, and allowing the alarm module to give an alarm to remind the human body of changing the sleep state until the sleep state of the human body is normal.

DETAILED DESCRIPTION

Figure 1A:
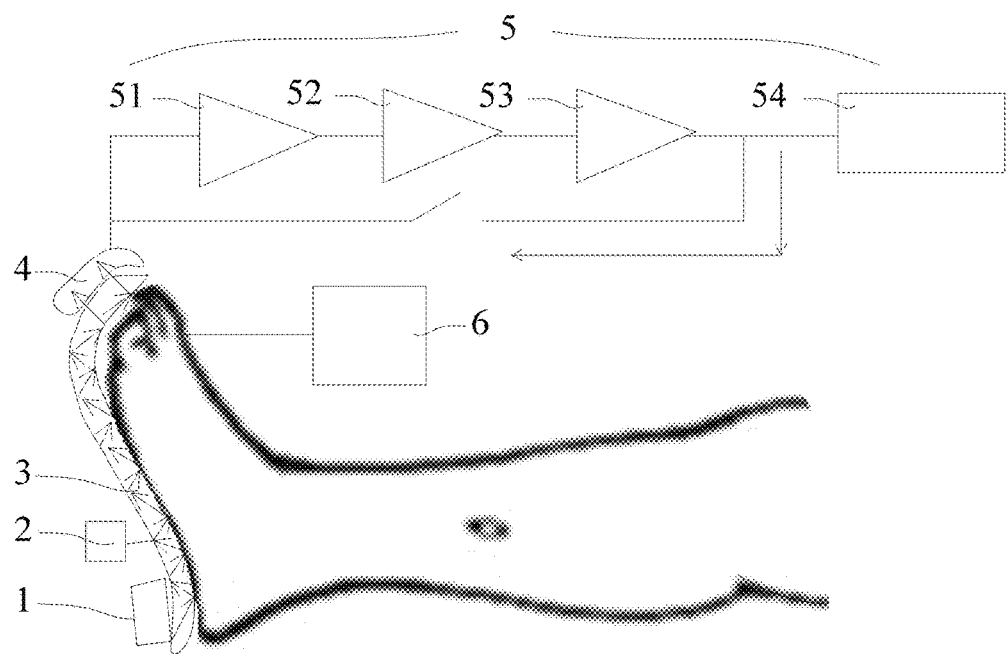
FIGS. 1a to 1b are schematic structural views of a human sleep monitoring device provided by the present disclosure.

The technical solutions of the embodiments will be described in a clearly and fully understandable way in connection with the drawings related to the embodiments of the invention. Apparently, the described embodiments are just a part but not all of the embodiments of the invention. Based on the described embodiments herein, those skilled in the art can obtain other embodiment(s), without any inventive work, which should be within the scope of the invention.

As illustrated in FIG. 1, the embodiment of the present disclosure provides a human sleep monitoring device, which comprises a signal processing module 5, an alarm module 6, a reflecting film 3 and a detection light emitting module 1 mounted on the reflecting film 3 and a receiving module 4.

The detection light emitting module 1 is configured to emit light which can be absorbed by the human body, e.g., laser, infrared light and near infrared light, to the human body. The detection light emitting module 1, for instance, may be achieved by a laser, an infrared generator, etc. Optionally, the detection light emitting module 1 may also be achieved by a near-infrared tunable fiber laser and an infrared transmitting tube. In the infrared transmitting tube, a luminophor is formed by infrared light-emitting diodes (LEDs) array. In the infrared LED, PN junctions are formed by materials with high infrared radiant efficiency, and additionally, a forward bias is adopted to inject current into the PN junctions so as to excite infrared light. The infrared LED is generally made from gallium arsenide (GaAs) and gallium aluminum arsenide (GaAlAs) and sealed by fully illuminating, light blue or black resins.

The reflecting film 3 is configured to guide sensitive light, which is emitted by the detection light emitting module 1 and not absorbed by the human body, to the receiving module 4. The main body of the reflecting film 3 is flaky and may have the shape of or an approximate shape of a detected body part, e.g., is in the form of plastics (PET, PMMA, PC and the like). A reflecting surface of the reflecting film may be a metallic reflective film and may also be an all-dielectric reflecting film, and alternatively, may also be a metallic dielectric reflecting film formed by combining both. Wherein, the metallic reflecting film is usually made from aluminum in ultraviolet regions, made from aluminum and silver in visible regions, and made from gold, silver, copper and the like in infrared regions. As the materials such as aluminum, silver and copper are likely to be oxidized in air and hence the performances can be reduced, the dielectric film must be adopted for protection. The common protective film materials include silicon oxide, magnesium fluoride, silicon dioxide, aluminum oxide, etc.

Optionally, in order to further improve the reflectivity of the metallic reflecting film, for instance, several dielectric layers with certain thickness may be additionally coated on the outside of the film to form the metallic dielectric reflecting film.

Figure 1B:
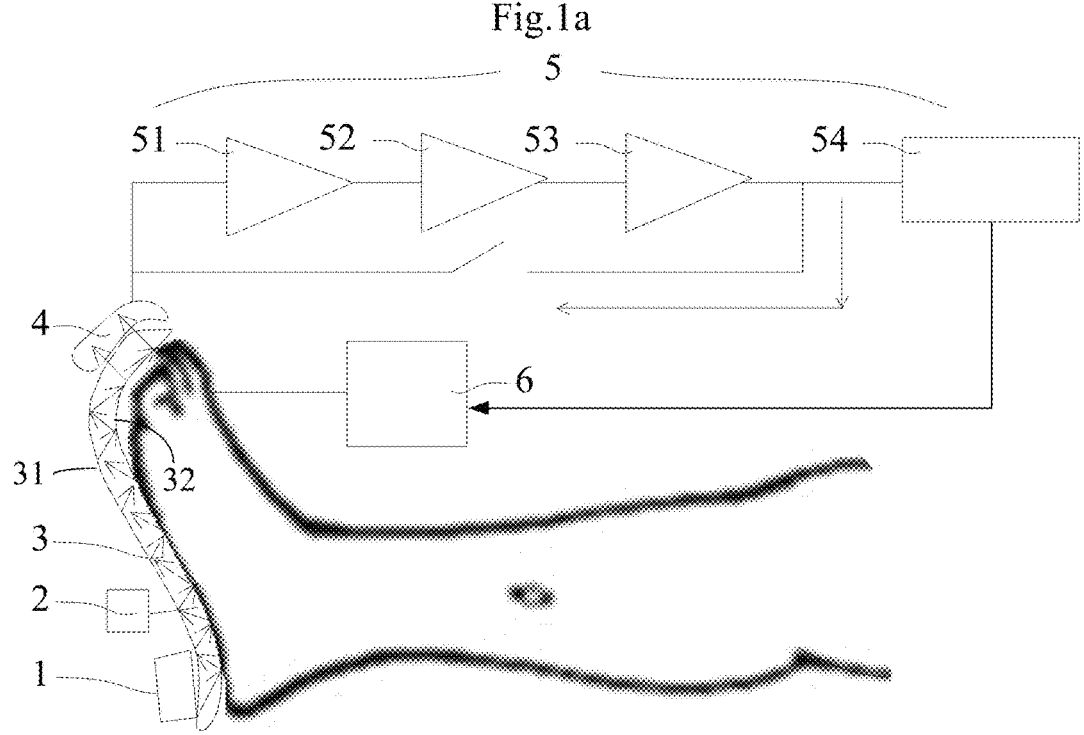

In one example of the present disclosure, the reflecting film 3 is provided with a human body contact surface 32 making contact with the human body. At least partial human body contact surface 32 is an illuminating surface. The detection light emitting module 1 and the receiving module 4 are mounted on an external surface of a deviated human body contact surface 31 of the reflecting film 3. An internal surface of the deviated human body contact surface 31 of the reflecting film 3 is a reflecting surface so as to fully reflect the part irradiated to the reflecting film 3 of the sensitive light in the reflecting film 3. In the embodiments as shown in FIGS. 1a and 1b, non-illuminate surface portions of the human body contact surface 32, for instance, correspond to arch or toe parts. The non-illuminate surface portions are also reflecting surfaces. Thus, these portions, for instance, have the light guide function so as to guide detection light from other portions to the receiving module 4, etc.

The receiving module 4 is configured to receive light which is not absorbed by the human body and reflected back from the reflecting film 3. Optionally, in one example, the receiving module, for instance, may be achieved by a photoreceiver. The photoreceiver includes a receiving antenna which can collect light fields propagated in space and converge the light fields to a surface of a detector. Thus, the information carried by optical carriers can be recovered at minimal additional noise and distortion. For instance, the photoreceiver may also be configured to amplify and shape received optical signals and regenerate original transmission signals.

The signal processing module 5 is connected with the receiving module 4 and configured to obtain physical sign data of the human body according to intensity information of the sensitive light received by the receiving module 4. The signal processing module 5, for instance, may be achieved by a microprocessor chip for the receiving, analyzing and processing of signals. For instance, optical signals received by the receiving module 4 are subjected to noise or interference filtering and converted into electric signals which can be easily analyzed and recognized. Optionally, the signal processing module may also include a memory, a sensor and the like as required, which are used for storing and detecting signals.

In one example provided by the present disclosure, as illustrated in FIG. 1, the signal processing module 5 may include a photoelectric converter 51, an amplifier 52 and a data converter 53. The signal processing module acquires systole data information according to the intensity information of the sensitive light received by the receiving module 4, compares the acquired systole data information with the systole data information in the normal sleep state of the human body, and sends an alarm signal to the alarm module 6 in the case of abnormal acquired systole data information, and the alarm module 6 gives an alarm when receiving the alarm signal.

The alarm module 6 gives an alarm when receiving the alarm signal, for instance, may give an alarm by speaker sound, LED light display, etc.

In the human sleep monitoring device, the detection light emitting module 1 is configured to emit sensitive light which can be absorbed by the human blood; after the sensitive light enters the reflecting film 3, the sensitive light runs through the illuminating surface of the reflecting film making contact with the human body and is irradiated to the human body and absorbed by the human blood; and the sensitive light which is not absorbed is fully reflected when irradiated to the reflecting film 3 and finally guided to the receiving module 4 by the reflecting film 3. In the sleep state of the human body, the blood flow volume of the human body will have certain rules according to the cardiac status. For instance, in the case of systole, the blood flow volume of the human body is reduced, and the sensitive light emitted by the detection light emitting module 1 is rarely absorbed by the human blood and mostly guided to the signal receiving module 4 by the reflecting film 3; and in the case of cardiectasis, the blood flow volume of the human body is increased, and the sensitive light emitted by the detection light emitting module 1 is mostly absorbed by the human blood and rarely guided to the receiving module 4 by the reflecting film 3. After a period of time, the signal processing module 5 will obtain the systole frequency dynamic distribution in the sleep state of the human body according to the intensity rule of the sensitive light received by the receiving module 4, and hence obtain the systole data information. Subsequently, the signal processing module 5 compares the obtained systole data information with the systole data in the normal sleep state of the human body. In the case of abnormal situation, the sleep state of the human body is determined to be abnormal, and the signal processing module 5 will send an alarm signal to the alarm module 6, and the alarm module 6 will give an alarm, so that the sleep state of the human body can be changed until the sleep state of the human body is normal.

Therefore, the human sleep monitoring device can monitor the sleep state of the human body in real time and remind the user in the case of abnormal sleep state of the human body until the sleep state of the human body is normal, and hence can improve the sleep effect of the human body.

In one example of the present disclosure, in order to process the light received by the receiving module 4 in the human sleep monitoring device, the receiving module 4 is connected with the signal processing module 5. As illustrated in FIG. 1, the signal processing module 5 includes: a photoelectric converter 51, an amplifier 52 and a data converter 53.

The photoelectric converter 51 is in signal connection with the receiving module 4 and configured to convert the intensity information of the light received by the signal receiving module 4 into current intensity information. In the case of high intensity of the light received by the receiving module 4, the current intensity obtained by the photoelectric converter 51 is high. In the case of low intensity of the light received by the receiving module 4, the current intensity obtained by the photoelectric converter 51 is low.

The amplifier 52 is in signal connection with the photoelectric converter 51 and configured to amplify the current information obtained by the amplifier 52 from the photoelectric converter 51 into recognizable degree. The current intensity obtained by the photoelectric converter 51 can be easily recognized after being amplified by the amplifier 52, which is conducive to information reading.

The data converter 53 is in signal connection with the amplifier 52 and configured to convert the amplified current information obtained by the amplifier 52 into data information. The data converter 53 converts the current information into the data information, which facilitates the subsequent data comparison and hence facilitates operation.

In the case of high intensity of the light received by the receiving module 4, the current intensity obtained by the photoelectric converter 51 is high. At this point, the amount of light absorbed by the human blood is small; the blood flow volume of the human body is low; and the situation of systole occurs. In the case of low intensity of the light received by the receiving module 4, the current intensity obtained by the photoelectric converter 51 is low; the current intensity amplified by the amplifier 52 is low; and hence the data obtained after the conversion of the data converter 53 is small. At this point, the amount of light absorbed by the human blood is large; the blood flow volume of the human body is high; and the situation of cardiectasis occurs. Thus, the intensity rules of the light absorbed by the human blood can reflect the systole frequency dynamic distribution in the sleep state of the human body, and hence the systole data information can be obtained.

As illustrated in FIG. 1, the signal processing module 5 may also include a data processing unit 54. The data processing unit 54 is in signal connection with the alarm module 6. The data processing unit 54 controls the alarm module 6 to take action when determining that the sleep state of the human body is abnormal. For example, the data information obtained by the data processing unit 54 is compared with the normal human sleep data stored in the data processing unit 54. When the comparison result indicates that the sleep state of the human body is abnormal, the signal processing module 5 will send an alarm signal to the alarm module 6. After receiving the signal, the alarm module 6 implements remind action, so that the sleep state of the human body can be changed until the sleep state of the human body is normal.

In one example of the present disclosure, the alarm module 6 is a vibrator for the alarm module 6 in the human sleep monitoring device to be able to give an alarm after receiving the alarm signal of the signal processing module 5. After receiving the alarm sent by the signal processing module 5, the vibrator operates and reminds the human body, so that the sleep state of the human body can be changed until the sleep state of the human body is normal.

In another example of the present disclosure, for the detection light emitting module 1 in the human sleep monitoring device to be able to emit the sensitive light capable of being absorbed by the blood, the detection light emitting module 1 may be an infrared emitter and may also be other emitters which can emit the sensitive light capable of being absorbed by the blood. In the sleep state of the human body, the blood flow volume of the human body will have certain rules according to the cardiac status. For instance, in the case of systole, the blood flow volume of the human body is reduced, and the sensitive light emitted by the detection light emitting module 1 is rarely absorbed by the human blood and mostly guided to the signal receiving module 4 by the reflecting film 3; and in the case of cardiectasis, the blood flow volume of the human body is increased, and the sensitive light emitted by the detection light emitting module 1 is mostly absorbed by the human blood and rarely guided to the receiving module 4 by the reflecting film 3. After a period of time, the signal processing module 5 will obtain the systole frequency dynamic distribution in the sleep state of the human body according to the intensity rules of the sensitive light received by the receiver, and hence obtain the systole data information. Subsequently, the signal processing module 5 compares the obtained systole data information with the systole data in the normal sleep state of the human body. In the case of abnormal situation, the sleep state of the human body is determined to be abnormal, and the signal processing module 5 will send an alarm signal to the alarm module 6, and the alarm module 6 operates so that the sleep state of the human body can be changed until the sleep state of the human body is normal.

In one example of the present disclosure, in order to avoid the excessive influence on the human sleep and monitor the human sleep more conveniently, the human body contact surface of the reflecting film may be used for covering the sole of the human body.

Figure 2:
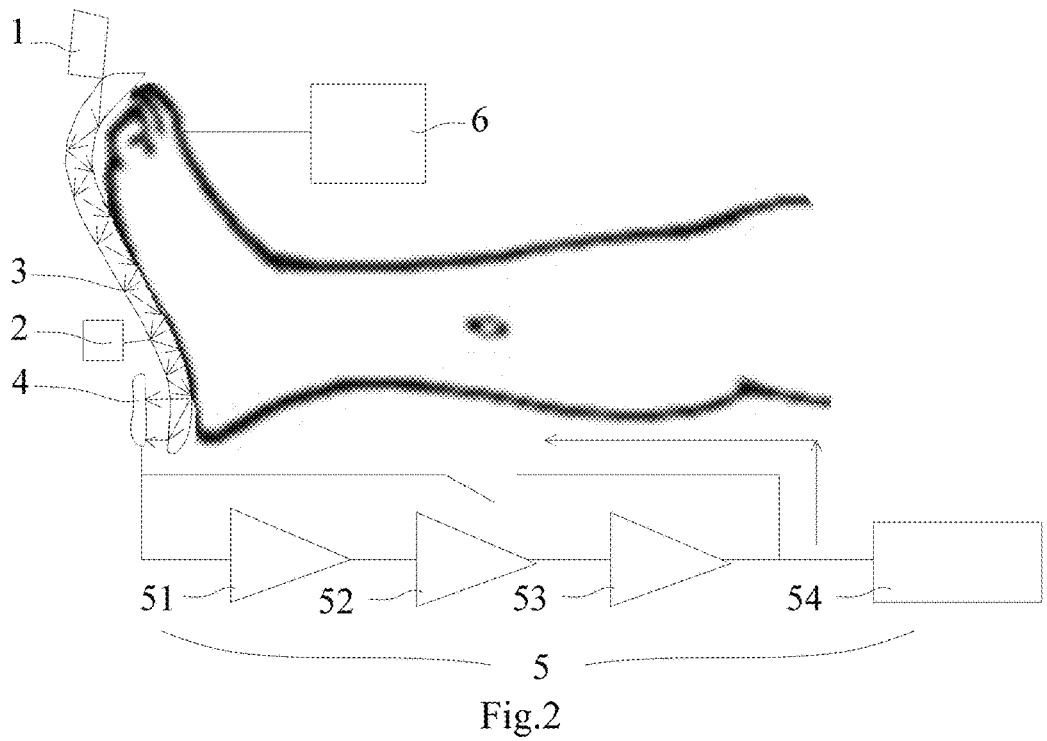
FIG. 2 is another schematic structural view of the human sleep monitoring device provided by the present disclosure.

For instance, in the human sleep monitoring device, the setting positions of the detection light emitting module 1 and the receiving module 4 on the reflecting film 3 may have a plurality of options. For instance, in one mode, as illustrated in FIG. 1, the detection light emitting module 1 may be mounted on a portion of the reflecting film 3 for covering the heel, and the receiving module 4 is mounted on a portion of the reflecting film 3 for covering the toes; and in another mode, as illustrated in FIG. 2, the detection light emitting module 1 may also be mounted on a portion of the reflecting film 3 for covering the toes, and the receiving module 4 is mounted on a portion of the reflecting film 3 for covering the heel. The detection light emitting module 1 emits the sensitive light capable of being absorbed by the human blood. One part of the light is absorbed by the blood on the feet, and other light not absorbed by the blood on the feet is reflected in the reflecting film 3 and finally guided to the receiving module 4. When more light is absorbed by the blood on the feet, less light is guided to the receiving module 4. At this point, the blood flow volume of the feet is increased, and the situation of cardiectasis occurs. When less light is absorbed by the blood on the feet, more light is guided to the receiving module 4. At this point, the blood flow volume of the feet is reduced, and the situation of systole occurs. The intensity rules of the light absorbed by the blood can reflect the systole frequency dynamic distribution in the sleep state of the human body, and hence the systole data information can be obtained.

In one example of the present disclosure, in order to achieve the function of monitoring the sleep state of the human body in real time and hence reminding the user of changing the sleeping posture of the human body to be normal and meanwhile achieve the objective of monitoring whether there are potential diseases in the human body and achieving massage sleep aid through phototherapy, in the human sleep monitoring device, as illustrated in FIG. 1, the human sleep monitoring device may further comprise: at least one physiotherapy module 2 mounted on the reflecting film 3. Each physiotherapy module 2 is in signal connection with the signal processing module 5. The signal processing module 5 is also configured to determine the health status of the human organ according to the information received by the receiving module 4, and control corresponding physiotherapy module 2 to give a physical therapy to corresponding acupoints of the sole when determining that one organ is diseased. When the signal processing module 5 determines that the sleep state of the human body is normal, the signal processing module 5 does not send an alarm signal to the alarm module 6, and the alarm module 6 does not take action. The signal processing module 5 compares the data obtained by the data processing unit 54 with the standard data, and hence determines whether the physical function is healthy. When determining that the physical function is unhealthy, the signal processing module 5 obtains a diseased organ and sends an action signal to the physiotherapy module 2, and subsequently, different phototherapy is performed at different acupoints of the sole. Thus, whether there are other potential diseases in the human body is monitored, and phototherapy and massage sleep aid can be achieved by phototherapy.

For instance, each physiotherapy module 2 is a physiotherapy light emitting module. After receiving the action signal sent by the signal processing module 5, each physiotherapy light emitting module sends physiotherapy light with corresponding wavelength to corresponding acupoints for irradiation, so as to achieve the objective of phototherapy.

For instance, each physiotherapy module 2 is a massage module. After receiving the action signal sent by the signal processing module 5, the massage module sends light with different wavelengths to the acupoints of the sole for irradiation, so as to achieve the objective of massage sleep aid.

For instance, at least one physiotherapy module 2 includes a plurality of physiotherapy modules 2. Each physiotherapy module is used for giving a physical therapy to one acupoint of the sole. After receiving the action signal sent by the signal processing module 5, different physiotherapy light emitting module sends physiotherapy light with different wavelengths to different acupoints, so as to achieve the objectives of phototherapy and massage sleep aid.

Figure 3:
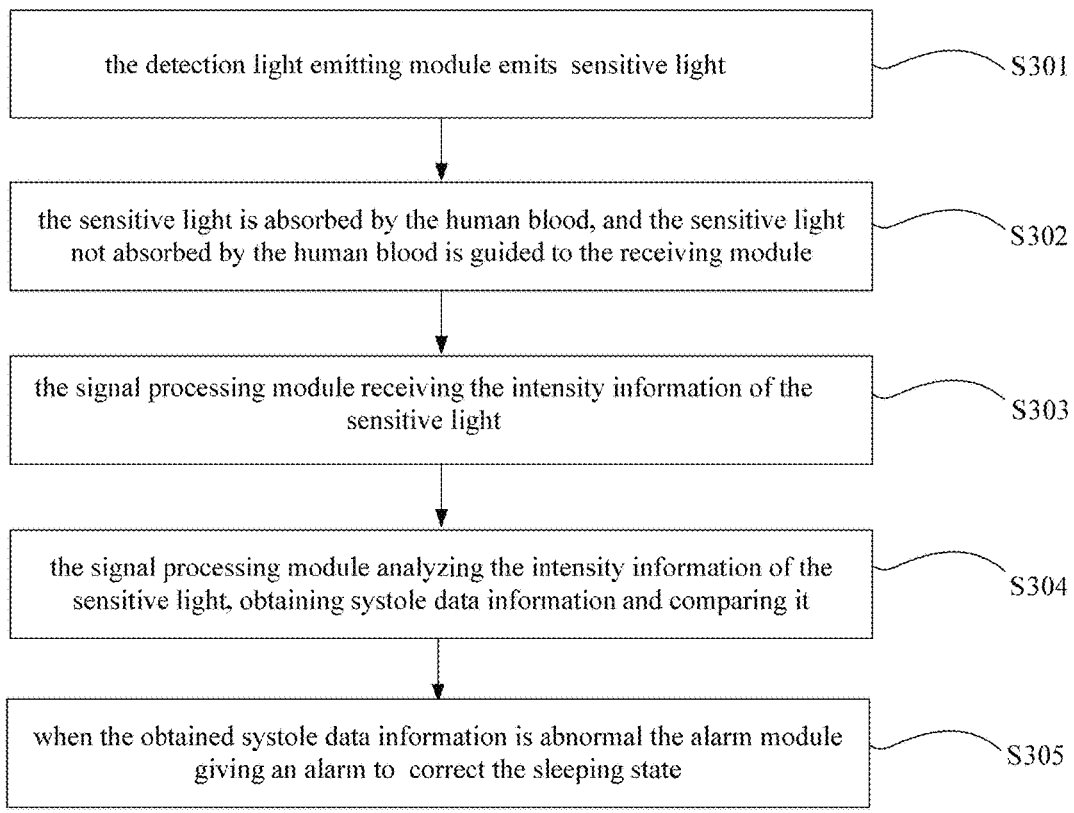
FIG. 3 is a flowchart of a monitoring method of the human sleep monitoring device, provided by the present disclosure.

In order to allow the human sleep monitoring device to monitor the human sleep in real time, remind the user in the abnormal sleep state of the human body until the sleep state of the human body is normal, and be able to improve the human sleep effect, as illustrated in FIG. 3, the monitoring method of the human sleep monitoring device, provided by the embodiment of the present disclosure, comprises the following steps:

S301: allowing the detection light emitting module 1 to emit the sensitive light, which can be easily absorbed by the human body, to the human body.

S302: allowing the sensitive light to run through the reflecting surface of the reflecting film 3, enter the reflecting film 3, be irradiated to the human body through the illuminating surface of the reflecting film 3, and be absorbed by the human blood, and allowing the sensitive light not absorbed by the human blood to return back to the reflecting film 3 and be irradiated to the reflecting surface and guided to the receiving module 4 through the total reflection of the reflecting surface.

S303: allowing the receiving module 4 to transmit the intensity information of the received sensitive light to the signal processing module 5.

S304: allowing the signal processing module 5 to analyze the intensity information of the sensitive light, obtain the systole data information, and compare the obtained systole data information with the systole data information in the normal sleep state of the human body.

S305: allowing the signal processing module 5 to send an alarm signal to the alarm module 6 when the obtained systole data information is abnormal, and allowing the alarm module 6 to give an alarm to remind the human body of correcting the sleeping posture until the sleep state of the human body is normal.

When the method is adopted to monitor the sleep state of the human body in real time, the blood flow volume of the human body has certain rules in the sleep state of the human body. For instance, in the case of systole, the blood flow volume of the human body is reduced, and the sensitive light emitted by the detection light emitting module 1 is rarely absorbed by the human blood and mostly guided to the signal receiving module 4 by the reflecting film 3; and in the case of cardiectasis, the blood flow volume of the human body is increased, and the sensitive light emitted by the detection light emitting module 1 is mostly absorbed by the human blood and rarely guided to the receiving module 4 by the reflecting film 3. Therefore, in the step S304, the signal processing module 5 will obtain the systole frequency dynamic distribution in the sleep state of the human body according to the intensity rules of the sensitive light received by the receiving module 4, and hence obtain the systole data information. In the step S305, the signal processing module 5 will compare the obtained systole data information with the systole data in the normal sleep state of the human body. In the case of abnormal situation, the sleep state of the human body is determined to be abnormal, and the signal processing module 5 will send an alarm signal to the alarm module 6, and the alarm module 6 will give an alarm, so that the sleep state of the human body can be changed until the sleep state of the human body is normal.

Therefore, the monitoring method of the human sleep monitoring device is adopted to monitor the human sleep in real time and remind the user in the case of abnormal sleep state of the human body until the sleep state of the human body is normal, and hence achieves the objective of improving the human sleep effect.

In the description of this specification, specific features, structures, materials or characteristic can be combined in appropriate means in any one or more embodiments or examples. Those skilled in the art can make various modifications and variations to the present disclosure without departing from the spirit and scope thereof. Thus, if these modifications and variations of the present disclosure are within the scope of the claims of the invention as well as their equivalents, the present disclosure is also intended to include these modifications and variations.

What are described above is related to the illustrative embodiments of the disclosure only and not limitative to the scope of the disclosure. Obvious variations and replacement by any one of the skilled person in the art in the technical scope of the disclosure should be all covered in the scope of this disclosure, therefore, the scopes of the disclosure are defined by the accompanying claims.

The application claims priority to the Chinese patent application No. 201510521048.1, filed on Aug. 21, 2015, the disclosure of which is incorporated herein by reference as part of the application.

What is claimed is:

1. A human sleep monitoring device, comprising a signal processing module, a reflecting film, a detection light emitting module and a receiving module, wherein the detection light emitting module is configured to emit detection light to the human body;

the reflecting film has an illuminating surface and a reflecting surface, partial light emitted by the detection light emitting module is absorbed by the human body based on the illuminating surface, and partial light which is emitted by the detection light emitting module and not absorbed by the human body is guided based on the reflecting surface to the receiving module;

the receiving module is configured to receive the light guided by the reflecting film and not absorbed by the human body; and the signal processing module is configured to obtain physiological sign data of the human body according to intensity information of the light received by the receiving module.

2. The device according to claim 1, wherein the reflecting film comprises a human body contact surface making contact with the human body and a deviated human body contact surface not making contact with the human body; at least partial human body contact surface is the illuminating surface; an internal surface of the deviated human body contact surface is the reflecting surface; the detection light emitting module and the receiving module are mounted on an external surface of the deviated human body contact surface of the reflecting film; and the internal surface of the deviated human body contact surface fully reflects the light irradiated into the reflecting film on the internal surface.

3. The human sleep monitoring device according to claim 2, wherein the human body contact surface of the reflecting film is used for covering the sole of the human body.

4. The device according to claim 1, wherein the physiological sign data of the human body include systole data information; and the signal processing module compares the obtained systole data information with the systole data information in the normal sleep state of the human body, and obtains the health status information of the human body.

5. The device according to claim 4, further comprising an alarm module, wherein the signal processing module sends an alarm signal to the alarm module in response to abnormal obtained systole data information, and the alarm module gives an alarm according to the received alarm signal.

6. The human sleep monitoring device according to claim 5, wherein the alarm module is a vibration alarm.

7. The human sleep monitoring device according to claim 1, wherein the signal processing module comprises:
 a photoelectric converter connected with the receiving module and configured to convert the intensity information of the light received by the receiving module into current intensity information;
 an amplifier connected with the photoelectric converter and configured to amplify the current information received by the photoelectric converter into recognizable degree;
 a data converter connected with the amplifier and configured to convert the amplified current information obtained by the amplifier into data information; and
 a data processing unit connected with the data converter and configured to process the information received by the data converter.

8. The human sleep monitoring device according to claim 7, further comprising an alarm module, wherein the data processing unit is connected with the alarm module and sends an alarm signal to the alarm module when determining that the sleep state of the human body is abnormal according to the data converted by the data converter.

9. The human sleep monitoring device according to claim 1, wherein the detection light emitting module is an infrared emitter.

10. The human sleep monitoring device according to claim 1, wherein the detection light emitting module is mounted on a portion of the reflecting film disposed on the heel, and the receiving module is mounted on a portion of the reflecting film disposed on the toes.

11. The human sleep monitoring device according to claim 1, further comprising:
 at least one physiotherapy module mounted on the reflecting film, wherein
 each physiotherapy module is connected with the signal processing module; and
 the signal processing module is also configured to determine the health status of the human organ according to the information received by the receiving module, and control corresponding physiotherapy module to give a physical therapy to the sole when determining that an organ is diseased.

12. The human sleep monitoring device according to claim 11, wherein each physiotherapy module is a physiotherapy light emitting module.

13. The human sleep monitoring device according to claim 11, wherein each physiotherapy module is a massage module.

14. The human sleep monitoring device according to claim 11, wherein at least one physiotherapy module comprises a plurality of physiotherapy module, and each physiotherapy module is used for giving a physical therapy to one acupoint of the sole.

15. A monitoring method of the human sleep monitoring device, comprising:
 allowing the detection light emitting module to emit light, which can be absorbed by the human body, to the human body;
 allowing the light emitted by the detection light emitting module to run through the surface of the reflecting film, enter the reflecting film and be irradiated to the human body through the reflecting film, allowing partial light emitted by the detection light emitting module to be absorbed by the human body based on an illuminating surface of the reflecting film, and allowing partial light not absorbed by the human body to be guided to the receiving module through a reflecting surface of the reflecting film;
 allowing the receiving module to transmit the intensity information of the received partial light which is not absorbed by the human body to the signal processing module; and
 allowing the signal processing module to analyze the intensity information of the light, obtain the systole data information, and compare the obtained systole data information with the systole data information in the normal sleep state of the human body.

16. The monitoring method according to claim 15, further comprising:
 allowing the signal processing module to send an alarm signal to the alarm module when the obtained systole data information is abnormal, and allowing the alarm module to give an alarm to remind the human body of changing the sleep state until the sleep state of the human body is normal.

* * * * *